(12) United States Patent
Burdulis

(10) Patent No.: US 8,518,092 B2
(45) Date of Patent: Aug. 27, 2013

(54) HARD TISSUE ANCHORS AND DELIVERY DEVICES

(75) Inventor: Albert G. Burdulis, San Francisco, CA (US)

(73) Assignee: Spinal Modulation, Inc., Menlo Park, CA (US)

( * ) Notice: Subject to any disclaimer, the term of this patent is extended or adjusted under 35 U.S.C. 154(b) by 0 days.

(21) Appl. No.: 13/175,488

(22) Filed: Jul. 1, 2011

(65) Prior Publication Data

US 2011/0257693 A1    Oct. 20, 2011

Related U.S. Application Data

(63) Continuation of application No. 11/952,081, filed on Dec. 6, 2007, now abandoned.

(60) Provisional application No. 60/873,549, filed on Dec. 6, 2006.

(51) Int. Cl.
*A61B 18/00* (2006.01)
*A61N 1/05* (2006.01)

(52) U.S. Cl.
USPC .......................................... 606/329; 607/117

(58) Field of Classification Search
USPC .......................... 606/300, 301, 329; 607/117
See application file for complete search history.

(56) References Cited

U.S. PATENT DOCUMENTS

| | | | |
|---|---|---|---|
| 525,891 A * | 9/1894 | Fricke | 174/154 |
| 3,724,467 A | 4/1973 | Avery et al. | |
| 3,845,770 A | 11/1974 | Theeuwes et al. | |
| 3,916,899 A | 11/1975 | Theeuwes et al. | |
| 4,141,367 A | 2/1979 | Ferreira | |
| 4,232,679 A | 11/1980 | Schulman | |
| 4,298,003 A | 11/1981 | Theeuwes et al. | |
| 4,313,448 A | 2/1982 | Stokes | |
| 4,374,527 A | 2/1983 | Iversen | |
| 4,479,491 A * | 10/1984 | Martin | 606/279 |
| 4,549,556 A * | 10/1985 | Tarjan et al. | 607/117 |
| 4,573,481 A | 3/1986 | Bullara | |
| 4,577,642 A | 3/1986 | Stokes | |
| 4,590,946 A | 5/1986 | Loeb | |

(Continued)

FOREIGN PATENT DOCUMENTS

| | | |
|---|---|---|
| CN | 2401143 Y | 10/2000 |
| EP | 0779080 A | 6/1997 |

(Continued)

OTHER PUBLICATIONS

Kim et al.; U.S. Appl. No. 13/402,786 entitled "Neurostimulation System," filed Feb. 22, 2012.

(Continued)

*Primary Examiner* — Kevin T Truong
*Assistant Examiner* — Christian Sevilla
(74) *Attorney, Agent, or Firm* — Shay Glenn LLP

(57) ABSTRACT

The present invention provides devices, systems and methods for anchoring medical devices to hard tissues, such as bones or bony structures, particularly vertebrae. By anchoring these medical devices directly to the surrounding hard tissue, the devices are anchored closer to the source of treatment. This provides additional stability and reduces migration of the device at the treatment site. Also, by attaching to hard tissue rather than soft tissue, a stronger attachment is often able to be made.

11 Claims, 8 Drawing Sheets

(56) References Cited

U.S. PATENT DOCUMENTS

| | | | |
|---|---|---|---|
| 4,607,639 A | 8/1986 | Tanagho et al. |
| 4,739,764 A | 4/1988 | Lue et al. |
| 4,786,155 A | 11/1988 | Fantone et al. |
| 4,803,988 A | 2/1989 | Thomson |
| 4,920,979 A | 5/1990 | Bullara |
| 4,940,065 A | 7/1990 | Tanagho et al. |
| 5,135,525 A | 8/1992 | Biscoping et al. |
| 5,270,099 A | 12/1993 | Kamiyama et al. |
| 5,299,569 A | 4/1994 | Wernicke et al. |
| 5,344,438 A | 9/1994 | Testerman et al. |
| 5,358,514 A | 10/1994 | Schulman et al. |
| 5,370,644 A | 12/1994 | Langberg |
| 5,411,537 A | 5/1995 | Munshi et al. |
| 5,411,540 A | 5/1995 | Edell et al. |
| 5,417,719 A | 5/1995 | Hull et al. |
| 5,458,626 A | 10/1995 | Krause |
| 5,489,294 A | 2/1996 | McVenes et al. |
| 5,505,201 A | 4/1996 | Grill et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,733,322 A | 3/1998 | Starkebaum |
| 5,741,319 A | 4/1998 | Woloszko et al. |
| 5,755,750 A | 5/1998 | Petruska et al. |
| 5,807,339 A | 9/1998 | Bostrom et al. |
| 5,824,021 A | 10/1998 | Rise |
| 5,865,843 A | 2/1999 | Baudino |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,983,141 A | 11/1999 | Sluijter et al. |
| 5,984,896 A | 11/1999 | Boyd |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A | 8/2000 | Alo et al. |
| 6,120,467 A | 9/2000 | Schallhorn |
| 6,161,048 A | 12/2000 | Sluijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,902 B1 | 3/2001 | Boveja |
| 6,214,016 B1 | 4/2001 | Williams et al. |
| 6,259,952 B1 | 7/2001 | Sluijter et al. |
| 6,298,256 B1 | 10/2001 | Meyer |
| 6,314,325 B1 | 11/2001 | Fitz |
| 6,319,241 B1 * | 11/2001 | King et al. ........... 604/502 |
| 6,349,233 B1 | 2/2002 | Adams |
| 6,353,762 B1 | 3/2002 | Baudino et al. |
| 6,356,786 B1 | 3/2002 | Rezai et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,425,887 B1 | 7/2002 | McGuckin et al. |
| 6,438,423 B1 | 8/2002 | Rezai et al. |
| 6,440,090 B1 | 8/2002 | Schallhorn |
| 6,466,821 B1 | 10/2002 | Pianca et al. |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 6,605,094 B1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,748,276 B1 | 6/2004 | Daignault, Jr. et al. |
| 6,754,539 B1 | 6/2004 | Erickson et al. |
| 6,788,975 B1 | 9/2004 | Whitehurst et al. |
| 6,792,318 B2 | 9/2004 | Chitre et al. |
| 6,832,115 B2 | 12/2004 | Borkan |
| 6,835,194 B2 | 12/2004 | Johnson et al. |
| 6,839,588 B1 | 1/2005 | Rudy |
| 6,862,479 B1 | 3/2005 | Whitehurst et al. |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,971,391 B1 | 12/2005 | Wang et al. |
| 6,978,180 B2 | 12/2005 | Tadlock |
| 7,096,070 B1 | 8/2006 | Jenkins et al. |
| 7,127,287 B2 | 10/2006 | Duncan et al. |
| 7,333,857 B2 | 2/2008 | Campbell |
| 7,337,005 B2 | 2/2008 | Kim et al. |
| 7,337,006 B2 | 2/2008 | Kim et al. |
| 7,447,546 B2 | 11/2008 | Kim et al. |
| 7,450,993 B2 | 11/2008 | Kim et al. |
| 7,502,651 B2 | 3/2009 | Kim et al. |
| 7,580,753 B2 | 8/2009 | Kim et al. |
| 2001/0003799 A1 | 6/2001 | Boveja |
| 2002/0077684 A1 | 6/2002 | Clemens et al. |
| 2002/0116030 A1 | 8/2002 | Rezai |
| 2002/0128694 A1 | 9/2002 | Holsheimer |
| 2002/0147486 A1 | 10/2002 | Soukup et al. |
| 2003/0018367 A1 | 1/2003 | Dilorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0088301 A1 | 5/2003 | King |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2004/0015202 A1 | 1/2004 | Chandler et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1 | 11/2004 | Cates et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052827 A1 | 3/2006 | Kim et al. |
| 2006/0052836 A1 | 3/2006 | Kim et al. |
| 2006/0052856 A1 | 3/2006 | Kim et al. |
| 2006/0064150 A1 | 3/2006 | Heist et al. |
| 2006/0089609 A1 | 4/2006 | Bleich et al. |

| | | |
|---|---|---|
| 2006/0095088 A1 | 5/2006 | DeRidder |
| 2006/0155344 A1 | 7/2006 | Rezai et al. |
| 2006/0195169 A1 | 8/2006 | Gross et al. |
| 2006/0206118 A1 | 9/2006 | Kim et al. |
| 2006/0241716 A1 | 10/2006 | Finch et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0119711 A1 | 5/2008 | Nikumb et al. |
| 2008/0140152 A1 | 6/2008 | Imran et al. |
| 2008/0140153 A1 | 6/2008 | Burdulis |
| 2008/0140169 A1 | 6/2008 | Imran |
| 2008/0147156 A1 | 6/2008 | Imran |
| 2008/0167698 A1 | 7/2008 | Kim et al. |
| 2008/0183221 A1 | 7/2008 | Burdulis |
| 2008/0183257 A1 | 7/2008 | Imran et al. |
| 2008/0188916 A1 | 8/2008 | Jones et al. |
| 2009/0210041 A1 | 8/2009 | Kim et al. |
| 2010/0137938 A1 | 6/2010 | Kishawi et al. |
| 2010/0179562 A1 | 7/2010 | Linker et al. |
| 2010/0249875 A1 | 9/2010 | Kishawi et al. |
| 2010/0292769 A1 | 11/2010 | Brounstein et al. |
| 2012/0158094 A1 | 6/2012 | Kramer et al. |
| 2012/0277839 A1 | 11/2012 | Kramer et al. |
| 2012/0283697 A1 | 11/2012 | Kim et al. |
| 2012/0310140 A1 | 12/2012 | Kramer et al. |

FOREIGN PATENT DOCUMENTS

| | | |
|---|---|---|
| EP | 1304135 A2 | 4/2003 |
| JP | 8080353 A | 3/1996 |
| JP | 10243954 A | 9/1998 |
| JP | 2004512105 | 4/2004 |
| JP | 2005516697 | 6/2005 |
| WO | WO 02/096512 A1 | 12/2002 |
| WO | WO 03/043690 A1 | 5/2003 |
| WO | WO 03/063692 | 8/2003 |
| WO | WO 03/066154 A2 | 8/2003 |
| WO | WO 03/090599 A2 | 11/2003 |
| WO | WO 2005/092432 A1 | 10/2005 |
| WO | WO 2006/084635 A2 | 8/2006 |

OTHER PUBLICATIONS

Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.
Abdulla et al.; Axotomy—and autotomy-induced changes in the excitability of rat dorsal root ganglion neurons; J Neurophysiol. 85(2); pp. 630-643; Feb. 2001.
Advanced Neuromodulation Systems, Inc. (ANSI) Research Briefing dated Aug. 20, 2004 by Stephens Inc. Investment Bankers pp. 1-4.
Advanced Neuromodulation Systems, Inc. (ANSI) Research Bulletin dated Jul. 2, 2004 by Stephens Inc. Investment Bankers pp. 1-7.
Advanced Neuromodulation Systems, Inc. (ANSI) Research Bulletin dated Jul. 27, 2004 by Stephens Inc. Investment Bankers pp. 1-9.
Advanced Neuromodulation Systems, Inc. Equity Research dated Jan. 16, 2003 by Pacific Growth Equities pp. 1-8.
Alo, Kenneth M. 2002. New Trends in Neuromodulation for the Management of Neuropathic Pain. Neurosurgery. 50 (4): 690-703.
Aoki, Yasuchika et al. 2004. Distribution and Immunocytochemical Characterization of Dorsal Root Ganglion Neurons Innervating the Lumbar Intervertebral Disc in Rats: A Review. Life Sciences. 74 (21): 2627-2642.
Askar, Zahid, et al. 2003. Scott Wiring for Direct Repair of Lumbar Spondylolysis. Spine. 28 (4): 354-357.
Baba, Hiroshi et al. 1999. Peripheral Inflammation Facilitates A? Fiber-Mediated Synaptic Input to the Substantia Gelatinosa of the Adult Rat Spinal Cord. The Journal of Neuroscience. 19 (2): 859-867.

Bajwa, Zahid H. et al. 2001. Herpetic Neuralgia: Use of Combination Therapy for Pain Relief in Acute and Chronic Herpes Zoster. Geriatrics. 56 (12): 18-24.
Barendse, G.A. et al. 2001. Randomized Controlled Trial of Percutaneo Intradiscal Radiofrequency Thermocoagulation for Chronic Discogenic Back Pain: Lack of Effect From a 90-Second 70 C Lesion. Spine. 26 (3): 287-92. (Abstract Only).
Barlocher, C.B. et al. 2003. Kryorhizotomy: An Alternative Technique for Lumbar Medial Branch Rhizotomy in Lumbar Facet Syndrome. J Neurosurg. 98 (1): 14-20. (Abstract Only).
Blau, A. et al. 1997. Characterization and Optimization of Microelectrode Arrays for In Vivo Nerve Signal Recording and Stimulation. Biosens Bioelectron.12 (9-10): 883-92. (Abstract Only).
Boston Scientific A Neuromodulation Primer dated Jun. 9, 2004 in Medical Supplies and Devices, published by Susquehanna Financial Group, LLLP pp. 1-17.
Brammah, T.B. et al. 1994. Syringomyelia as a Complication of Spinal Arachnoiditis. Spine. 19 (22): 2603-5. (Abstract Only).
Braverman D.L. et al. 2001. Using Gabapentin to Treat Failed Back Surgery Syndrome Caused by Epidural Fibrosis: A Report of 2 Cases. Arch Phys Med Rehabil. 82 (5): 691-3. (Abstract Only).
Burton et al.; The organization of the seventh lumbar spinal ganglion of the cat; J Comp Neurol.; 149(2); pp. 215-232; May 15, 1973.
Carlton, Susan M. et al. 2001. Tonic Control of Peripheral Cutaneo Nociceptors by Somatostatin Receptors. Journal of Neuroscience. 21 (11): 4042-4049.
Chaplan, S.R. et al. 1994. Quantitative Assessment of Tactile Allodynia in the Rat Paw. Journal of Neuroscience Methods. 53 (1): 55-63.
Cho, J. 1997. Percutaneo Radiofrequency Lumbar Facet Rhizotomy in Mechanical Low Back Pain Syndrome. Stereotact Funct Neurosurg. 68 (1-4): 212-7. (Abstract Only).
Crampon, M.-A. et al. 2002. Nerve Cuff Electrode With Shape Memory Alloy Armature: Design and Fabrication. Bio-Medical Materials and Engineering. 12 (4): 397-410.
Cuoco, Jr., Frank A. et al. 2000. Measurement of External Pressures Generated by Nerve Cuff Electrodes. IEEE Transactions on Rehabilitation Engineering. 8 (1): 35-41.
Cyberonics, Inc. Equity Research dated Jan. 16, 2003 by Pacific Growth Equities pp. 1-14.
Denny, N.M. et al. 2003. Evaluation of an Insulated Tuohy Needle System for the Placement of Interscalene Brachial Plex Catheters. Anaesthesia. 58 (6): 554-7. (Abstract Only).
Dreyfuss, Paul et al. 2000. Efficacy and Validity of Radiofrequency Neurotomy for Chronic Lumbar Zygapophysial Joint Pain. Spine. 25 (10): 1270-1277.
Dubuisson, D. 1995. Treatment of Occipital Neuralgia by Partial Posterior Rhizotomy at C1-3. J Neurosurg. 82 (4): 581-6. (Abstract Only).
Eschenfelder, Sebastian et al. 2000. Dorsal Root Section Elicits Signs of Neuropathic Pain Rather than Reversing Them in Rats With L5 Spinal Nerve Injury. Pain. 87 (2): 213-219.
Firth, Ava et al. 1999. Development of a Scale to Evaluate Postoperative Pain in Dogs. J Am Vet Med Assoc. 214 (5): 651-659.
Garcia Cosamalon, P. J. et al. 1991. Dorsal Percutaneo Radiofrequency Rhizotomy Guided With CT Scan in Intercostal Neuralgias. Technical note. Acta Neurochir (Wien). 109 (3-4): 140-1.
Giorgi, C. et al. 1984. Surgical Treatment of Glossopharyngeal Neuralgia and Pain From Cancer of the Nasopharynx. A 20-Year Experience. J Neurosurg. 61 (5): 952-5. (Abs. Only).
Gocer, A.I. et al. 1997. Percutaneo Radiofrequency Rhizotomy of Lumbar Spinal Facets the Results of 46 cases. Neurosurg Rev. 20 (2): 114-6. (Abstract Only).
Haller, H. et al. Treatment of Chronic Neuropathic Pain After Traumatic Central Cervical Cord Lesion with Gabapentin. Journal of Neural Transmission. 110 (9): 977-981.
Herron, L.D. 1989. Selective Nerve Root Block in Patient Selection for Lumbar Surgery: Surgical Results. J Spinal Disord. 2 (2): 75-9. (Abstract Only).
Higuchi, Yoshinori, et al. 2002. Exposure of the Dorsal Root Ganglion in Rats to Pulsed Radiofrequency Currents Activates Dorsal Horn Lamina I and II Neurons. Neurosurgery. 50 (4): 850-856.

Holsheimer, J. et al. 1995. Effects of Electrode Geometry and Combination on Nerve Fibre Selectivity in Spinal Cord Stimulation. Medical & Biological Engineering & Computing. 33 (5): 676-682.

Igarashi, T. et al. 2004. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181-.

Julius, David et al. 2001. Molecular Mechanisms of Nociception. Nature. 413 (6852): 203-210.

Kanpolat, Yucel et al. 2001. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534.

Kapadia, N.P. et al. 2000. Gabapentin for Chronic Pain in Spinal Cord Injury: A Case Report. Arch Phys Med Rehabil. 81 (10): 1439-41. (Abstract Only).

Kapoor, Vibhu et al. 2003. Refractory Occipital Neuralgia: Preoperative Assessment With CT-Guided Nerve Block Prior to Dorsal Cervical Rhizotomy. American Journal of Neuroradiology. 24 (10): 2105-10.

Karai, Laszlo et al. 2004. Deletion of Vanilloid Receptor 1-Expressing Primary Afferent Neurons for Pain Control. Journal of Clinical Investigation. 113 (9): 1344-1352.

Kline, David G. et al. 1998. Management and Results of Sciatic Nerve Injuries: a 24-Year Experience. Journal of Neurosurgery. 89 (1): 13-23.

Kobayashi, Shigeru et al. 2004. Pathology of Lumbar Nerve Root Compression Part 1: Intraradicular Inflammatory Changes Induced by Mechanical Compression. Journal of Orthopaedic Research. 22 (1): 170-179.

Kobayashi, Shigeru et al. 2004. Pathology of Lumbar Nerve Root Compression Part 2: Morphological and Immunohistochemical Changes of Dorsal Root Ganglion. Journal of Orthopaedic Research. 22(1): 180-188.

Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.

Koszewski, W. et al. 2003. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only).

Lawrence, Stephen M. et al. 2002. Long-Term Biocompatibility of Implanted Polymer-Based Intrafascicular Electrodes. Journal of Biomedical Materials Research. 63 (5): 501-506.

Lee, In-Seop et al. 2002. Characterization of Iridium Film as a Stimulating Neural Electrode. Biomaterials. 23 (11): 2375-2380.

Lew, Henry L. et al. 2004. Preganglionic Approach to Transforaminal Epidural Steroid Injections. Am. J. Phys. Med. Rehabil. 83 (5): 378.

Lopez et al.; Excitatory and inhibitory effects of serotonin on spinal nociceptive reflexes are mediated by 5-HT2 and 5-HT1B receptors; (Database Biosis Biosciences information service, Philadelphia, PA, US, XP002567533, accession No. PREV200100573757); Abstract; 2001.

Ma et al.; Enhanced excitability of dissociated primary sensory neurons after chronic compression of the dorsal root ganglion in the rat; Pain; 113(1-2); pp. 106-112; Jan. 2005.

Maher, C.O. et al. 1999. Lateral Exit-Zone Stenosis and Lumbar Radiculopathy. J Neurosurg. 90 (1): 52-8. (Abstract Only).

Mailley, Sophie et al. 2004. Thin Film Platinum Cuff Electrodes for Neurostimulation: In Vitro Approach of Safe Neurostimulation Parameters. Bioelectrochemistry. 63: 359-364.

Masini, Michelle et al. 1996. Activated Pyrolytic Carbon Tip Pacing Leads: An Alternative to Steroid-Eluting Pacing Leads? PACE. 1: 1832-1835.

Medtronic, Inc. Equity Research dated Dec. 18, 2002 by Pacific Growth Equities pp. 1-20.

Medtronic. Analysis of Sales/Earnings-F1Q05: Many Gives and Takes in the Quarter dated Aug. 20, 2004 by Morgan Stanley pp. 1-25.

Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.

Modern Ideas: The Gate Control Theory of Chronic Pain. Spine-Health.com: Your Comprehensive Resource for Back Pain. http://www.spine-health.com/topics/cd/pain/chronic_paintheories/chronic_pain_theory02.html (accessed Feb. 24, 2006).

Mond, Harry G. et al. 2004. Implantable Transveno Pacing Leads: The Shape of Things to Come. PACE. 27: 887-893.

Monti, Enrico. 2004. Peripheral Nerve Stimulation: A Percutaneo Minimally Invasive Approach. Neuromodulation. 7 (3): 193. (Abstract Only).

Myles et al.; Effects of different methods of peripheral nerve repair on the number and distribution of muscle afferent neurons in rat dorsal root ganglion; J Neurosurg; 77(3); pp. 457-462; Sep. 1992.

Nannini et al.; Muscle recruitment with intrafascicular electrodes; IEEE Trans on Biomedical Engineering; vol. 38; No. 8; pp. 769-776 Aug. 1991.

Naples, Gregory G. 1988. A Spiral Nerve Cuff Electrode for Peripheral Nerve Stimulation. IEEE Transactions on Biomedical Engineering. 35 (11): 905-916.

Narozny, Martin et al. 2001. Therapeutic Efficacy of Selective Nerve Root Blocks in the Treatment of Lumbar Radicular Leg Pain. Swiss Med Wkly. 131 (5-6): 75-80.

Nashold, Blaine S. et al. 1979. Peripheral Nerve Stimulation for Pain Relief Using a Multicontact Electrode System. Technical note. Journal of Neurosurgery. 51 (6): 872-873.

Nashold, Blaine S. et al. 1982. Long-Term Pain Control by Direct Peripheral-Nerve Stimulation. The Journal of Bone and Joint Surgery. 64 (1): 1-10.

Neumann, Simona et al. 2002. Regeneration of Sensory Axons Within the Injured Spinal Cord Induced by Intraganglionic cAMP Elevation. Neuron. 34 (6): 885-93.

Nielson, K.D. et al. 1976. Peripheral Nerve Injury From Implantation of Chronic Stimulating Electrodes for Pain Control. Surg Neurol. 5 (1): 51-3. (Abstract Only).

North, Richard B. et al. 1991. Dorsal Root Ganglionectomy for Failed Back Surgery Syndrome: A 5-Year Follow-Up Study. J Neurosurg. 74: 236-242.

North, Richard B. et al. 2000. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company.

Nygaard, Oystein P. et al. 1998. The Function of Sensory Nerve Fibers in Lumbar Radiculopathy: Use of Quantitative Sensory Testing in the Exploration of Different Populations of Nerve Fibers and Dermatomes. Spine. 23 (3): 348-352.

Obata, K. et al. 2004. Activation of Extracellular Signal-Regulated Protein Kinase in the Dorsal Root Ganglion Following Inflammation Near the Nerve Cell Body. Neuroscience. 126 (4): 1011-1021.

Obata, Koichi, et al. 2002. Expression of Neurotrophic Factors in the Dorsal Root Ganglion in a Rat Model of Lumbar Disc Herniation. Pain. 99 (1-2): 121-132.

Olby, Natasha J. et al. 2001. Development of a Functional Scoring System in Dogs With Acute Spinal Cord Injuries. Am J Vet Res. 62 (10): 1624-1628.

Parlier-Cuau, Caroline et al. 1999. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513.

Pedrolli, C. et al. 1990. [Dorsolumbar Arachnoid Cysts. A Case Report]. Recenti Prog Med. 81 (11): 699-701. (Abstract Only).

Prats-Galino et al.; Representations of hindlimb digits in rat dorsal root ganglia; J Comp Neurol; 408(1); pp. 137-145; May 24, 1999.

Rodriguez, Francisco J. et al. 2000. Polyimide Cuff Electrodes for Peripheral Nerve Stimulation. Journal of Neuroscience Methods. 98 (2): 105-118.

Rokugo, Tomoyuki et al. 2002. A Histochemical Study of Substance P in the Rat Spinal Cord: Effect of Transcutaneo Electrical Nerve Stimulation. J Nippon Med Sch. 69 (5): 428-433.

Romero, E. et al. 2001. Neural Morphological Effects of Long-Term Implantation of the Self-Sizing Spiral Cuff Nerve Electrode. Medical & Biological Engineering & Computing. 39 (1): 90-100.

Rongstad, K. et al. 1996. Popliteal Sciatic Nerve Block for Postoperative Analgesia. Foot Ankle Int. 17 (7): 378-82. (Abstract Only).

Ruetten, S. et al. 2003. Endoscopic Surgery of the Lumbar Epidural Space (Epiduroscopy): Results of Therapeutic Intervention in 93 Patients. Minim Invasive Neurosurg. 46 (1): 1-4. (Abstract Only).

Sairyo, K. et al. 2003. A New Endoscopic Technique to Decompress Lumbar Nerve Roots Affected by Spondylolysis. Technical Note. J Neurosurg. 98 (3): 290-3. (Abstract Only).

Salame, K. et al. 2003. Surgical Treatment of Spasticity by Selective Posterior Rhizotomy 30 Years Experience. Isr Med Assoc J. 5 (8): 543-6. (Abstract Only).

Saris, S.C. et al. 1986. Sacrococcygeal Rhizotomy for Perineal Pain. Neurosurgery. 19 (5): 789-93. (Abstract Only).

Sauvage, P.J. et al. 2000. Intraspinal Synovial Cysts of the Lumbar Spine: Imaging Findings and Treatment by Percutaneo Steroid Injection. Review of 13 Cases. [Kystes Synoviaux Intraspinaux Lombaires: Imagerie et Traitement Par Infiltration. A Propos De.

Schwartzman, Robert J. et al. 2001. Neuropathic Central Pain: Epidemiology, Etiology, and Treatment Options. Arch Neurol. 58 (10): 1547-1550.

Sheth, Rishi N. et al. 2002. Mechanical Hyperalgesia After an L5 Ventral Rhizotomy or an L5 Ganglionectomy in the Rat. Pain. 96: 63-72.

Siddall, Philip J. et al. 2004. Persistent Pain as a Disease Entity: Implications for Clinical Management. Anesth Analg. 99: 510-20.

Silvers, H.R. 1990. Lumbar Percutaneo Facet Rhizotomy. Spine.15 (1): 36-40. (Abstract Only).

Slappendel, R. et al. 1997. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. (Abstract Only).

Sluijter, Menno E. et al. 1998. The Effects of Pulsed Radiofrequency Fields Applied to the Dorsal Root Ganglion—A Preliminary Report. The Pain Clinic.11 (2): 109-117.

Smith, H.P. et al. 1981. Radiofrequency Neurolysis in a Clinical Model: Neuropathological Correlation. J Neurosurg. 55 (2): 246-53. (Abstract Only).

Spaic, M. et al. 1999. Drez Surgery on Con Medullaris (After Failed Implantation of Vascular Omental Graft) for Treating Chronic Pain Due to Spine (Gunshot) Injuries. Acta Neurochir(Wein). 141(12): 1309-1312.

Spaic, M. et al. 2002. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462.

Stanton-Hicks, M. et al. 1997. Stimulation of the Central and Peripheral Nervo System for the Control of Pain. Journal of Clinical Neurophysiology. 14 (1): 46-62.

Steinbok, P. et al. 1998. Complications After Selective Posterior Rhizotomy for Spasticity in Children With Cerebral Palsy. Pediatr Neurosurg. 28 (6): 300-13. (Abstract Only).

Stolker, Robert J. et al. 1994. The Treatment of Chronic Thoracic Segmental Pain by Radiofrequency Percutaneo Partial Rhizotomy. J Neurosurg. 80 : 986-992.

Strait, T.A. et al. 1981. Intraspinal Extradural Sensory Rhizotomy in Patients With Failure of Lumbar Disc Surgery. J Neurosurg. 54 (2): 193-6. (Abstract Only).

Taha, J.M. et al. 1995. Long-Term Results of Radiofrequency Rhizotomy in the Treatment of Cluster Headache. Headache. 35 (4): 193-6. (Abstract Only).

Taub, Arthur et al. 1995. Dorsal Root Ganglionectomy for Intractable Monoradicular Sciatica: A Series of 61 Patients. Stereotact Funct Neurosurg. 65 (1-4): 106-110.

Uematsu, Sumio. 1988. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). P.

Van Zundert, Jan et al. 2005. Pulsed Radiofrequency in Chronic Pain Management: Looking for the Best Use of Electrical Current. World Institute of Pain. 5 (2): 74-76.

Van De Kraats, Everine B. et al. 2004. Noninvasive Magnetic Resonance to Three-Dimensional Rotational X-Ray Registration of Vertebral Bodies for Image-Guided Spine Surgery. Spine. 29 (3): 293-297.

Van Kleef, M. et al. 1993. Effects and Side Effects of a Percutaneo Thermal Lesion of the Dorsal Root Ganglion in Patients with Cervical Pain Syndrome. Pain. 52 (1): 49-53.

Van Kleef, M. et al. 1996. Radiofrequency Lesion Adjacent to the Dorsal Root Ganglion for Cervicobrachial Pain: A Prospective Double Blind Randomized Study. Neurosurgery. 38 (6): 1127-31.

Van Kleef, Maarten et al. 1998. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill.

Van Zundert, J. et al. 2005. Pulsed and Continuo Radiofrequency Current Adjacent to the Cervical Dorsal Root Ganglion of the Rat Induces Late Cellular Activity in the Dorsal Horn. Anesthesiology. 102 (1): 125-31.

Vaughan, R. 1975. Percutaneo Radiofrequency Gangliotomy in the Treatment of Trigeminal Neuralgia and Other Facial Pain. Aust N Z J Surg. 45 (2): 203-7. (Abstract Only).

Viton, J.-M. et al. 1998. Short-Term Assessment of Periradicular Corticosteroid Injections in Lumbar Radiculopathy Associated With Disc Pathology. Neuroradiology. 40 (1): 59-62.

Viton, J.M. et al. 1998. Short-Term Evaluation of Periradicular Corticosteroid Injections in the Treatment of Lumbar Radiculopathy Associated With Disc Disease. Rev Rhum Engl Ed. 65 (3): 195-200. (Abstract Only).

Wagner, A.L. et al. 2002. Selective Nerve Root Blocks. Tech Vasc Interv Radiol. 5 (4): 194-200. (Abstract Only).

Waxman et al.; Sodium channels, excitability of primary sensory neurons, and the molecular basis of pain; Muscle Nerve; 22(9); pp. 1177-1187; Sep. 1999.

Weiner, Richard L. 2000. The Future of Peripheral Nerve Neurostimulation. Neurological Research. 22 (3): 299-304.

Weiner, Richard L. 2003. Peripheral Nerve Neurostimulation. Neurosurgery Clinics of North America. 14 (3): 401-408.

Weinstein, James et al. 1988. The Pain of Discography. Spine. 13 (12):1344-8.

Wessels et al.; A rostrocaudal somatotopic organization in the brachial dorsal root ganglia of neonatal rats; Clin Neurol Neurosurg; 95 Suppl; pp. S3-11; 1993.

Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.

Wessels et al.; Somatotopic organization in the sensory innervation of the rat hindlimb during development, using half dorsal root ganglia as subsegmental units; Eur J Morphol; 28(2-4); pp. 394-403; 1990.

Wessels et al.; The rostrocaudal organization in the dorsal root ganglia of the rat: a consequence of plexus formation?; Anat Embryol (Berl); 190(1); pp. 1-11; Jul. 1994.

Wetzel, F. Todd et al. 1997. Extradural Sensory Rhizotomy in the Management of Chronic Lumbar Radiculopathy: A Minimum 2-Year Follow-up Study. Spine. 22 (19): 2283-2291.

Wetzel, F.T. 1992. Chronic Benign Cervical Pain Syndromes: Surgical Considerations. Spine. 17 (10): S367-74. (Abstract Only).

Wetzel, F.T. et al. 1992. The Treatment of Chronic Extremity Pain in Failed Lumbar Surgery. The Role of Lumbar Sympathectomy. Spine. 17 (12): 2367-8. (Abstract Only).

White, P.F. et al. 2003. The Use of a Continuo Popliteal Sciatic Nerve Block After Surgery Involving the Foot and Ankle: Does It Improve the Quality of Recovery? Anesth Analg. 97 (5): 1303-9. (Abstract Only).

Whitworth, Louis Anthony et al. 2002. Application of Spinal Ablative Techniques for the Treatment of Benign Chronic Painful Conditions. Spine. 27 (22): 2607-2612.

Wilkinson, H.A. et al. 2001. Sensory Ganglionectomy: Theory, Technical Aspects, and Clinical Experience. J Neurosurg. 95 (1): 61-6. (Abstract Only).

Wong, C.B. et al. 2002. Clinical Outcomes of Revision Lumbar Spinal Surgery: 124 Patient With a Minimum of Two Years of Follow-Up. Chang Gung Med J. 25 (3): 175-82. (Abstract Only).

Wright, Robert E. et al. 1998. Neurostimulation of the L2 Dorsal Root Ganglion for Intractable Disc Pain: Description of a Novel Technique. Presented at the IFESS.

Wu, Gang et al. 2001. Early Onset of Spontaneo Activity in Uninjured C-Fiber Nociceptors After Injury to Neighboring Nerve Fibers. Journal of Neuroscience. 21 (8): RC140.

Yamashita, Toshihiko et al. 2002. A Quantitative Analysis of Sensory Function in Lumbar Radiculopathy Using Current Perception Threshold Testing. Spine. 27 (14): 1567-1570.

Yoshida, Hirotoshi et al. 1997. Lumbar Nerve Root Compression Caused by Lumbar Intraspinal Gas: Report of Three Cases. Spine.22 (3): 348-351.

Young, R.F. 1996. Chapter 161: Dorsal Rhizotomy and Dorsal Root Ganglionectomy (pp. 3442-3451). Neurological Surgery 4th Edition. (Julian R. Youmans ed.). Philadelphia: W.B. Saunders Company.

Grigsby et al.; U.S. Appl. No. 13/104,787 entitled "Methods, systems and devices for reducing migration," filed May 10, 2011.

Sedan, R. et al. Therapeutic Electrical Neurostimulation. French Language Society of Neurosurgery—28th Annual Congress—Athens, May 29-30, 1978. Neurochirurgie. 24: 3-& Suppl. 1 (in French with English Summary pp. 121-125.).

Wedley et al. Handbook of Clinical Techniques in the Management of Chronic Pain. Taylor & Francis; pp. 17-19. Nov. 27, 1996.

\* cited by examiner

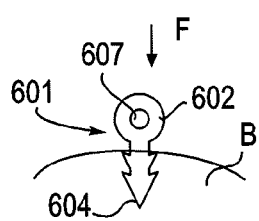
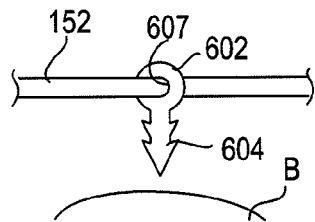
FIG. 3        FIG. 4
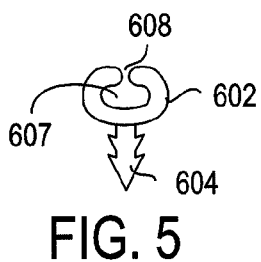
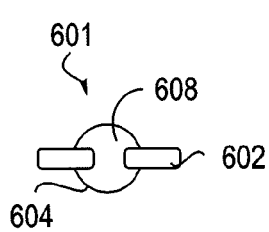
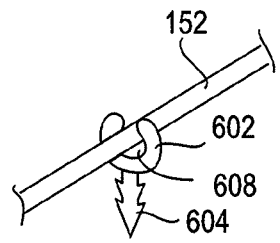
FIG. 5     FIG. 6     FIG. 7
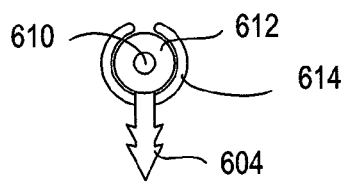
FIG. 8
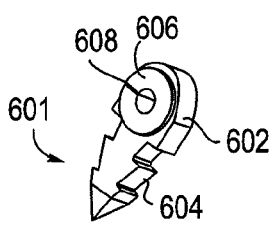
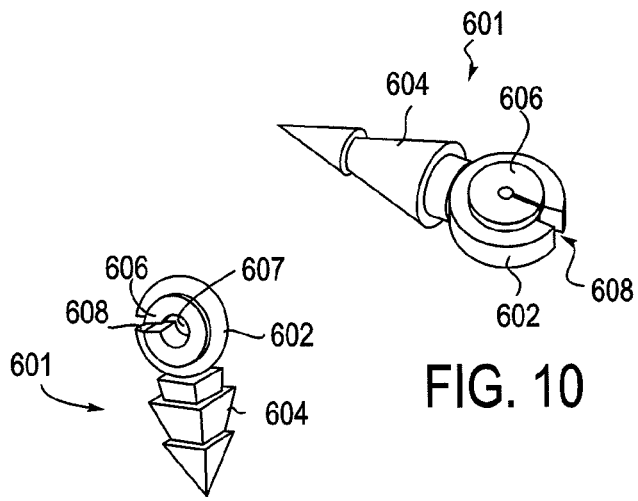
FIG. 9A     FIG. 9B     FIG. 10

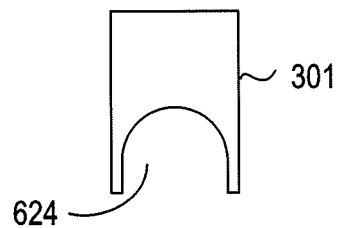
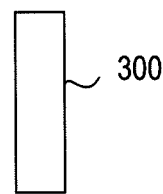
FIG. 15A    FIG. 15B
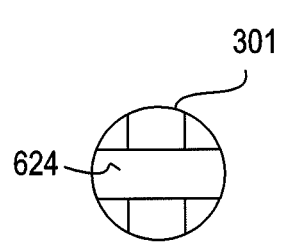
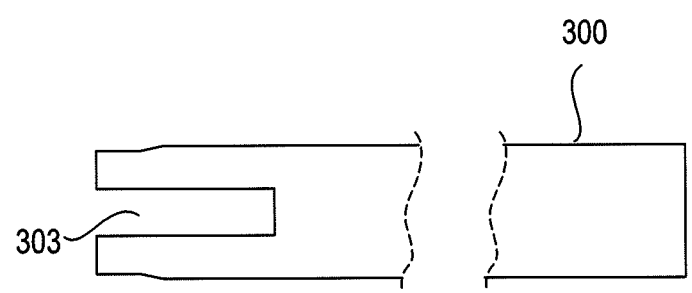
FIG. 15C    FIG. 15D
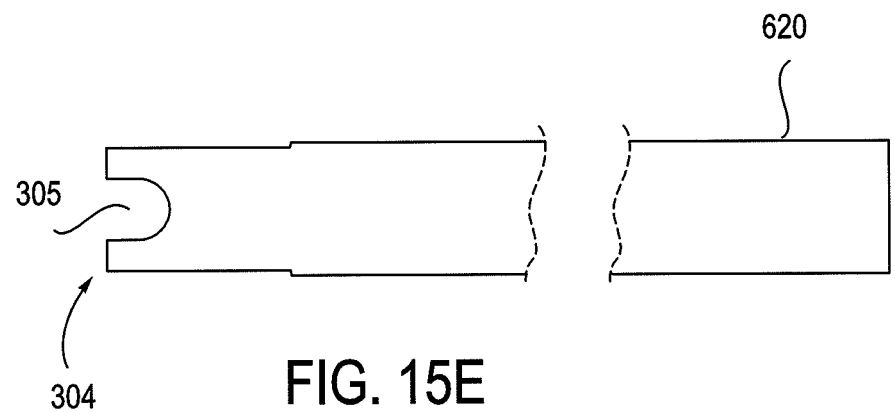
FIG. 15E

HARD TISSUE ANCHORS AND DELIVERY DEVICES

CROSS-REFERENCES TO RELATED APPLICATIONS

This application is a continuation of U.S. patent application Ser. No. 11/952,081, filed on Dec. 6, 2007 now abandoned, which claims priority of U.S. Provisional Patent Application No. 60/873,549, filed on Dec. 6, 2006, which is incorporated herein by reference for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

A variety of implantable medical devices are used to treat portions of the anatomy which reside near bones or bony structures within the body of a patient. Such devices are typically anchored in place by suturing portions of the device to surrounding soft tissue. Often the device includes suture holes designed specifically for this purpose at predetermined locations along the device. Thus, the device may only be sutured at these locations, limiting the areas and types of tissue available for suturing thereto. Often, the location is far from the treatment site. Such distance and instability of anchoring tissue can contribute to lead migration and pull-out.

For example, conventional spinal cord stimulators (SCS) are positioned along the spinal column to treat pain. A conventional SCS system comprises an implantable lead and an implantable power source or implantable pulse generator IPG. Using fluoroscopy, the lead is implanted into the epidural space of the spinal column and positioned against the dura layer of the spinal cord. The lead extends from the spinal column to the IPG which is remotely implanted. Typically, the lead is sutured to soft tissue remote from the point of entry into the epidural space. And, lead migration and pull-out are common problems associated with SCS.

Therefore, it is desired to provide a more stable anchoring system for implantable devices, such as leads. Such an anchoring system should provide anchoring at desired locations rather than merely at locations along the device which are predesigned for anchoring. Such anchoring should also assist in resisting migration and pull-out. At least some of these objectives will be met by the present invention.

BRIEF SUMMARY OF THE INVENTION

The present invention provides devices, systems and methods for anchoring medical devices to hard tissues, such as bones or bony structures, particularly vertebrae. A variety of medical devices are used to treat portions of the anatomy which reside near bones or bony structures within the body of a patient. The devices and systems of the present invention are suitable for use with many of such medical devices and specialized devices used for particular treatments. By anchoring these directly to the surrounding hard tissue, the devices are anchored closer to the source of treatment. This provides additional stability and reduces migration of the device at the treatment site. Also, by attaching to hard tissue rather than soft tissue, a stronger attachment is often able to be made.

In a first aspect of the present invention, a hard tissue anchor is provided for securing an element to a hard tissue. In some embodiments, the hard tissue comprises a penetrating end shaped for penetrating the hard tissue, and a head having an aperture, wherein the aperture is configured to receive the element therethrough and wherein the head is configured to secure the element within the aperture. Typically, the element comprises a lead, however catheters or other devices may be used.

In some embodiments, the head includes a channel connected to the aperture, wherein the channel is configured allow passage of the element from outside of the head to the aperture. In some instances, the head is adjustable to close the channel, such as by deformation of the head. Optionally, deformation of the head may secure the element within the aperture. In some embodiments, the head further comprises a grommet disposed within the aperture. The grommet may assist in holding the element within the aperture.

In some embodiments, the penetrating end has a tapered, conical, notched, barbed or serrated shape. In such instances, the hard tissue anchor is considered a tack and is pressed into the hard tissue. In other embodiments, the penetrating end has a shank with a helical thread. In these instances, the hard tissue anchor is considered a screw and is rotated into the hard tissue.

In a second aspect of the present invention, a method is provided for anchoring an element to a hard tissue in a body: In some embodiments, the method comprises advancing a hard tissue anchor toward the hard tissue, wherein the anchor has a penetrating end and a head having an aperture, positioning the element within the aperture, and applying pressure to the head so as to drive the penetrating end at least partially into the hard tissue.

In some embodiments, applying pressure comprises applying pressure to the head so as to secure the element within the aperture. Optionally, applying pressure comprises deforming the head so as to secure the element within the aperture due to friction.

In some instances, the method further comprises implanting the element in the body. Such implanting may occur before the positioning step of positioning the element within the aperture. This allows the hard tissue anchors to be utilized with existing implanted systems.

In still further embodiments, the anchor includes a channel connected to the aperture and the method further comprises passing a portion of the element through the channel to the aperture. Optionally, applying pressure comprises deforming the head so as to at least partially close the channel.

To deliver a hard tissue anchor of the present invention, such methods may include mounting the head of the anchor on a distal end of an applicator. In some situations, advancing the hard tissue anchor toward the hard tissue comprises advancing the distal end of the applicator through a percutaneous access opening. In such instances, the applicator has a low profile suitable for such percutaneous delivery.

In some embodiments, applying pressure to the head comprises applying pressure to the applicator. Optionally, applying pressure to the applicator may comprise deforming the head by force of the applicator so as to secure the element within the aperture due to friction.

In a third aspect of the present invention, an applicator is provided for delivering a hard tissue anchor. In some embodiments, the applicator comprises an elongate body having a proximal end and a distal end, wherein the distal end is configured to receive a head of the hard tissue anchor, and a handle attached to the proximal end of the elongate body so that force applied to the handle is translatable to the head of the hard tissue anchor. Optionally, the elongate body may be shaped for passage through a percutaneous access opening.

In some embodiments, the applicator further comprises a release button for releasing the hard tissue anchor from the distal end of the elongate body. The distal end may include a recess for receiving the head, from which the hard tissue anchor is releasable.

When the hard tissue anchor comprises a bone tack, the force typically comprises longitudinal force which is translatable to a downward force on the head of the hard tissue anchor. When the hard tissue anchor comprises a bone screw, the force typically comprises rotational force which is translatable to rotation of the head of the hard tissue anchor. In such instances, the distal end may comprise a rotatable member joinable with the head, wherein the rotation force rotates the rotatable member.

Other objects and advantages of the present invention will become apparent from the detailed description to follow, together with the accompanying drawings.

BRIEF DESCRIPTION OF THE DRAWINGS

FIG. 3 illustrates an embodiment of a bone tack of the present invention.

FIG. 4 illustrates an embodiment of a bone tack having an element threaded through its head prior to implantation of the element.

FIG. 5 illustrates a side view of a tack having a channel along the top of the head.

FIG. 6 illustrates a top view of such the tack of FIG. 5.

FIG. 7 illustrates passing an element through a channel in the head of a bone tack.

FIG. 8 illustrates a lead surrounded by a silicone tube positioned within arms of the head of a bone tack.

FIGS. 9A-9B illustrate an embodiment of a bone tack having a grommet.

FIG. 10 illustrates a tack having a grommet wherein the channel of the grommet has been closed by crimping of the head.

FIGS. 15A, 15B, 15C, 15D, 15E illustrates various views elongate body of an applicator having an insert positionable within its distal end.

DETAILED DESCRIPTION OF THE INVENTION

Figure 1:
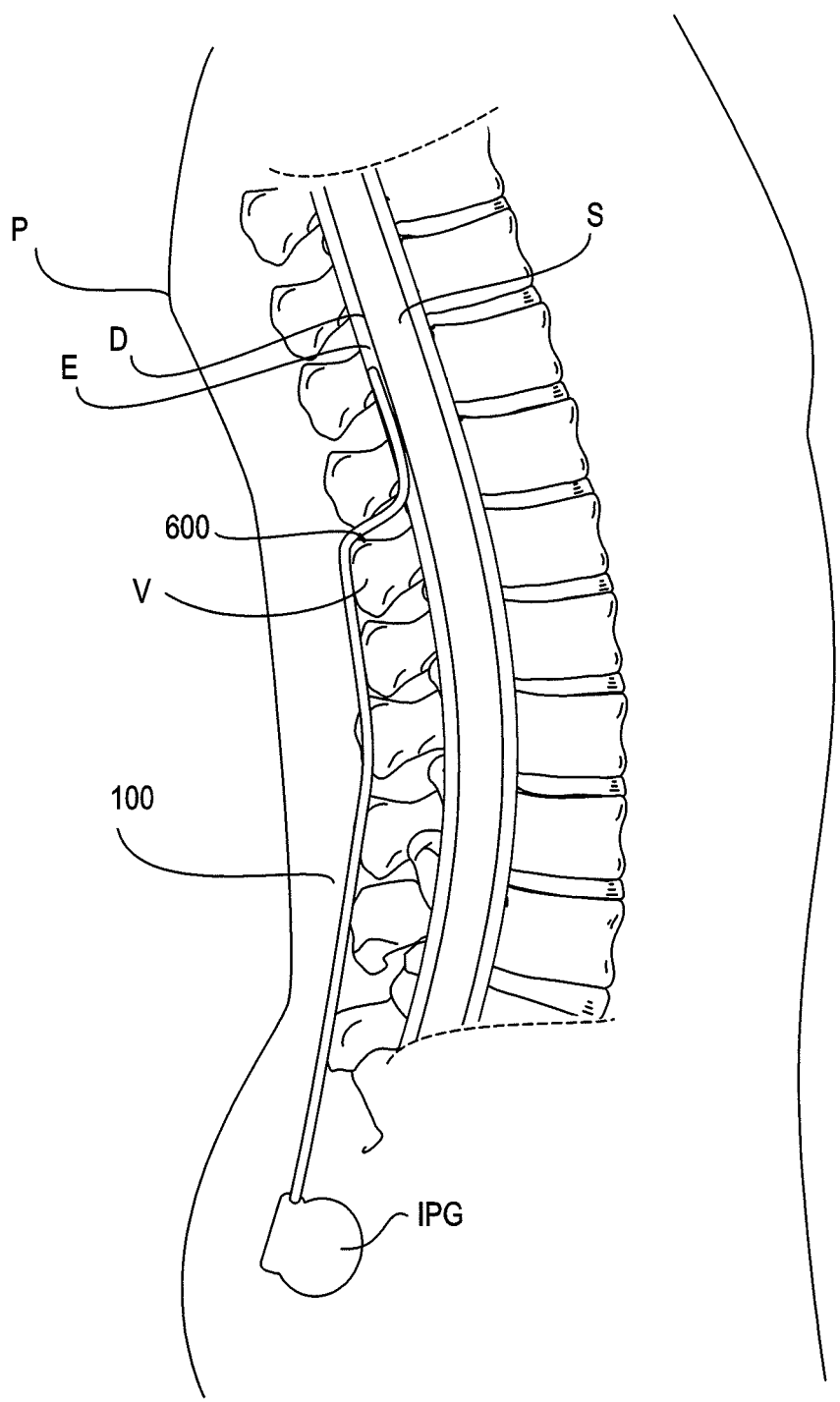
FIG. 1 illustrates a hard tissue anchor of the present invention used with a conventional SCS system.

The present invention provides devices, systems and methods for anchoring medical devices to hard tissues, such as bones or bony structures, particularly vertebrae. A variety of medical devices are used to treat portions of the anatomy which reside near bones or bony structures within the body of a patient. For example, spinal cord stimulators (SCS) are positioned along the spinal column to treat pain. FIG. 1 illustrates a conventional SCS system comprising an implantable lead 100 and an implantable power source or implantable pulse pulse generator IPG. Using fluoroscopy, the lead 100 is implanted into the epidural space E of the spinal column S and positioned against the dura layer of the spinal cord. The lead 100 is implanted either through the skin via an epidural needle (for percutaneous leads) or directly and surgically through a mini laminotomy operation (for paddle leads). In either case, the leads 100 extend from the spinal column S to the IPG which is remotely implanted. Typically, the leads 100 are sutured to soft tissue remote from the point of entry into the epidural space E. Such suturing is often insufficient to adequately the implanted lead 100, thus leading to migration or pull-out. FIG. 1 illustrates a hard tissue anchor 600 of the present invention used in conjunction with the conventional SCS system to anchor the implantable lead 100. As shown, the anchor 600 can be used to attach the lead 100 a hard tissue, such as a vertebrae V near the point of entry to the epidural space E. This provides more secure anchoring by fixing to a harder tissue and reduces the distance between the distal portion of the lead and the site of anchoring. This assists in reducing migration and pull-out of the lead 100.

Figure 2:
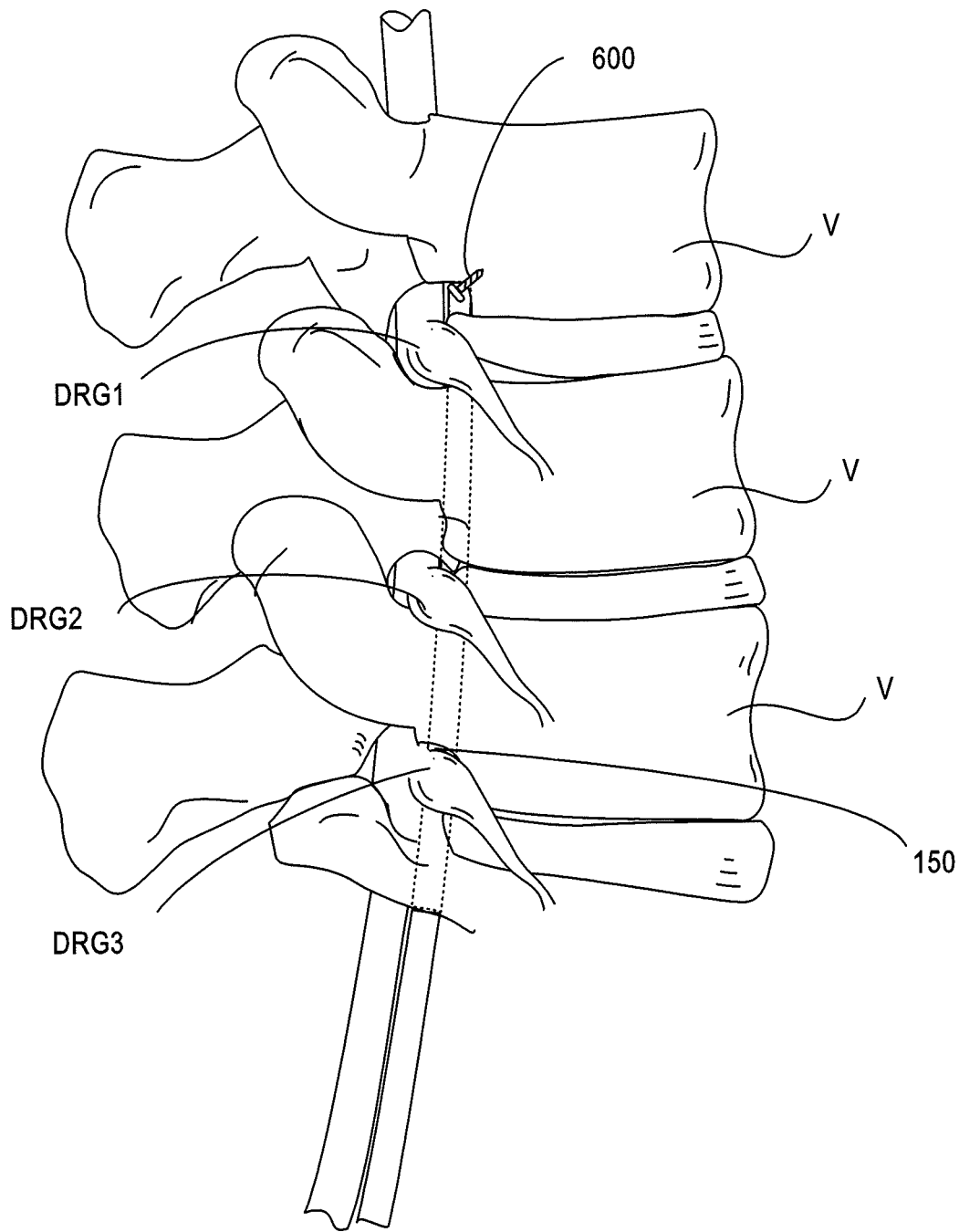
FIG. 2 illustrates a hard tissue anchor of the present invention used with a lead which is implanted near a DRG to provide selective stimulation thereto.

In addition, the devices, systems and methods of the present invention may be used to anchor other types of medical devices, in particular various other types of leads used to selectively stimulate the spinal anatomy, particularly the dorsal root or dorsal root ganglion (DRG). FIG. 2 illustrates a lead 150 which is implanted near a DRG to provide selective stimulation thereto. Examples of such leads are provided in U.S. patent application Ser. No. 11/952,049, filed Dec. 6, 2007, entitled "Grouped Leads For Spinal Stimulation", and U.S. patent application Ser. No. 11/952,053, filed Dec. 6, 2007, entitled "Grouped Leads For Posterior Access Of Directed Spinal Stimulation", both incorporated herein by reference. As shown, a hard tissue anchor 600 of the present invention may be used to anchor the lead 150 to a portion of the vertebrae V which is near the DRG. This anchors the lead 150 close to the stimulation site and reduces migration or pull-out of the lead 150.

The hard tissue anchors 600 of the present invention include bone tacks and bone screws. FIG. 3 illustrates an embodiment of a bone tack 601 of the present invention. The bone tack 601 can be used to anchor an element, such as a lead or catheter, to a bone or bony structure, such as near to a site of an intended application. In this embodiment, the bone tack 601 has a head 602 and a penetrating end 604 opposite the head 602. The penetrating end 604 may have a tapered, conical, notched, barbed, serrated or otherwise shaped end which is suitable for penetrating bone B, as shown. The head 602 includes an aperture 607 through which the element 152 can be threaded prior to implantation of the element 152, as illustrated in FIG. 4. The bone tack 601 is advanced along the element 152 to the desired anchoring position. Force is then applied to the head 602 to advance the penetrating end 604 into the bone B, thereby fixing the element 152 to the bone B at that location. This may be achieved during the implantation procedure of the element 150.

Other embodiments of the bone tack 601 are particularly suited for anchoring the element 150 at an anchoring location when it is less desirable to pre-load the anchor on the element 150. This may be the case when the element 150 is already implanted or it is not possible to advance an anchor over the element 150, such as from one of the ends of the element 150 to the anchoring location. In some of these embodiments, the head 602 of the bone tack 601 includes a channel 608 which connects to the aperture 607. FIG. 5 illustrates a side view of an embodiment of a tack 601 having such a channel 608 along the top of the head 602, and FIG. 6 illustrates a top view of such a tack 601. The tack 601 can be slipped over the element 150 through the channel 608 in the head 602 so that the element 150 passes through the aperture 607, as illustrated in FIG. 7. Thus, the tack 601 can be positioned at any location along the element 150. The channel 608 can then be closed by deformation of the head 602. Further deformation of the head 602 crimps the head 602 onto the element 150 resisting relative motion.

FIG. 8 illustrates a lead 610 surrounded by a silicone tube 612 positioned within arms 614 of the head 602 of a bone tack 601. Deforming or crimping of the head 602 (at least one arm 614) holds the silicone tube 612 in relation to the head 602 and further crimping holds the lead 610 in relation to the silicone tube 612. Thus, various degrees of deformation may be used to provide differing desired results.

In some embodiments, the tack 601 includes a grommet 606, as illustrated in FIGS. 9A-9B. The grommet 606 includes a channel which is alignable with the channel 608 of the head 602. Thus, an element 150 may be passed through the channel 608 of the head 602 and the aligned channel of the grommet 606. The grommet 606 assists in applying friction to the element 150 and protects the element 150 from possible damage. Deformation or crimping of the head 602 applies further friction to the element 150, such as fixing the element 150 within the grommet 606. FIG. 10 illustrates a tack 601 having a grommet 606 wherein the channel of the grommet 606 has been closed by crimping of the head 602. This illustrates the reduction in size of the aperture an therefore increased friction against the element 150.

Figure 11A:
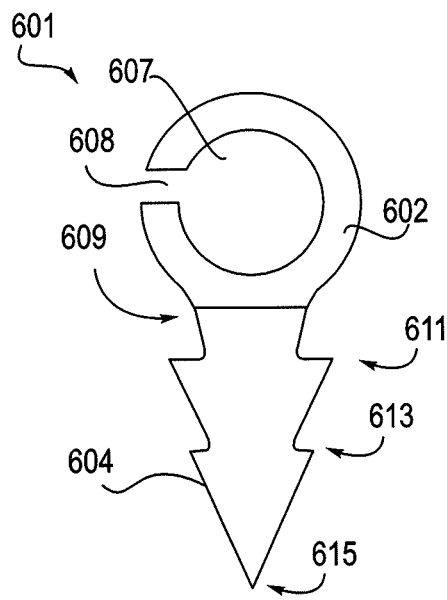
FIGS. 11A, 11B, 11C, 11D illustrate front, side, top and bottom views, respectively, of one embodiment of a bone tack of the present invention.
Figure 11B:
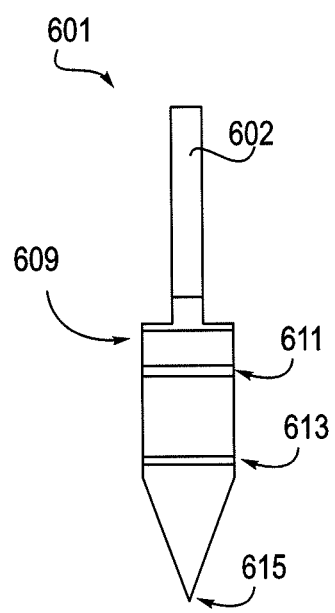
Figure 11C:
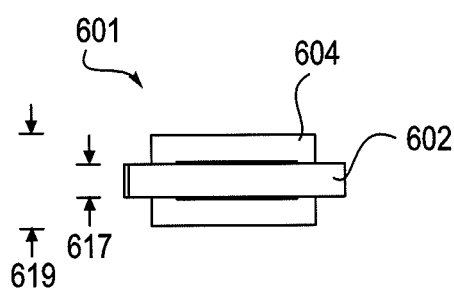
Figure 11D:
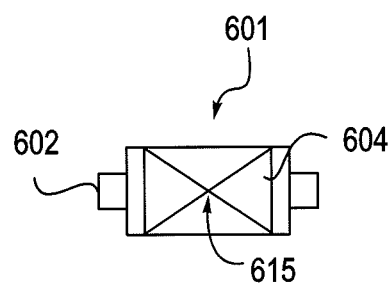

FIGS. 11A, 11B, 11C, 11D provide front, side, top and bottom views, respectively, of one embodiment of a bone tack 601 of the present invention. In the front view illustrated in FIG. 11A, tack 601 includes head 602 and penetrating end 604. As shown in FIG. 11A, head 602 can be shaped like an incomplete ring to include aperture 607 and channel 608. Head 602 can have a 0.060 inch diameter, aperture 607 can have a 0.040 inch diameter, and channel 608 can be 0.008 inches wide, for example. The penetrating end 604 can have serrations which taper from a first serration 611 to a second serration 613 to a point 615. For example, first serration 611 can have a width of approximately 0.045 inches and extend outwards at an angle of approximately 50 degrees, second serration can have a width of approximately 0.035 inches and extend outwards at an angle of approximately 50 degrees, and penetrating end 604 can have a length of approximately 0.105 inches from the center of aperture 607 to point 615. Additionally, the distance from the center of aperture 607 to neck 609 can be approximately 0.029 inches, the distance from the center of aperture 607 to first serration 611 can be approximately 0.043 inches, and the distance from the center of aperture 607 to second serration 613 can be approximately 0.068 inches. Neck 609 of the penetrating end 604 can attach to head 602, and can extend outwards at an angle of approximately 30 degrees. FIG. 11B shows a side view of bone tack 601, including head 602 and penetrating end 604 having first serration 611, second serration 613, and point 615. As shown in FIG. 11B, penetrating end 604 can come to a sharp point 615 at an angle of approximately 40 degrees. Furthermore, the distance from second serration 613 to point 615 can be approximately 0.034 inches, for example. FIG. 11C shows a top view of bone tack 601. Head 602 can have a depth of approximately 0.009 inches, and penetrating end 604 can have a depth of approximately 0.025 inches, for example. FIG. 11D illustrates point 615 of penetrating end 604. Thus, the bone tacks 601 of the present invention typically have a small size to allow positioning in confined or hard to reach areas of the anatomy. It may be appreciated that such dimensions are exemplary and are not intended to limit the scope of the present invention.

The head 602 and a penetrating end 604 are typically formed from the same material and may comprise any biocompatible and/or bioresorbable material including but not limited to cobalt chromium, cobalt chromium alloys, titanium, titanium alloys, stainless steel, resorbable PGA or PLA, and PEEK.

The grommet 606 may be comprised of any soft biocompatible and/or bioresorbable material including but not limited to silicone or polyurethane. The grommet 606 could be an assembly or molded onto the tack 606.

Figure 12:
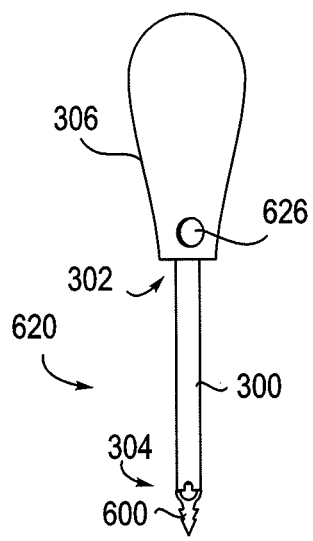
FIG. 12 illustrates an applicator for delivery of a bone tack to a portion of a hard tissue.

The bone tacks 601 of the present invention are driven into a portion of bone B by mechanical force, such as tapping or pressing. Referring to FIG. 12, an applicator 620 is provided for delivery of the bone tack 601 to a portion of a bone B. The applicator 620 is designed so that the tack 601 can be delivered through a percutaneous access opening and positioned at an anchoring location via fluoroscopy or other imaging techniques. Typically, the applicator 620 comprises an elongate body 300 with a low profile to assist in accessing a variety of target locations within the body. The elongate body 300 has a proximal end 302 and a distal end 304, wherein the distal end 304 is configured to receive the hard tissue anchor 600. In most embodiments, the applicator 620 also includes a handle 306 attached to the proximal end 302 of the elongate body 300.

Figure 13:
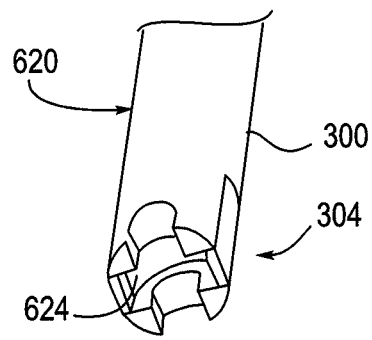
FIG. 13 illustrates a distal end of the applicator having a recess for receiving a head of a bone tack.
Figure 14:
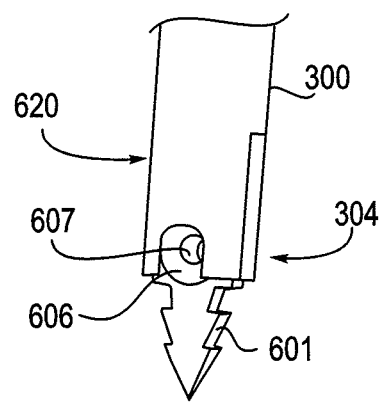
FIG. 14 illustrates a bone tack securely fixed to an applicator during insertion via friction fit with a grommet.

FIG. 13 illustrates an embodiment of a distal end 304 of the applicator 620 having a recess 624 for receiving a head 602 of a bone tack 601. In some embodiments, the bone tack 601 is securely fixed to the applicator 620 during insertion via friction fit with the grommet 606, as illustrated in FIG. 14. The tack 601 is penetrated and anchored into the bone B via the penetrating end 604, by application of downward or longitudinal force on the tack 601 by the applicator 620. Thus, force applied to the handle 306 is translatable to the head 602 of the hard tissue anchor 600 and drives the anchor 600 into the hard tissue. In some embodiments, such force also then crimps the head 602 onto an element passing through the aperture 607. The tack 601 can then be released from the applicator 620, such as with the use of a release button 626. The tack 601 is then left behind with the element passing therethrough.

In some embodiments, the distal end 304 is comprised of an insert that is inserted into the elongate body 300. FIGS. 15A-15E illustrate various views of an elongate body 300 having an insert 301. Typically the insert 301 is formed or machined so that together the insert 301 and the elongate body 300 desirably receive the bone tack 601. FIG. 15A illustrates a side view of an insert 301 having a recess 624 for receiving a bone tack 601. Here the recess 624 has a depth of 0.050 inches and a width of 0.060 inches. FIG. 15B illustrates an embodiment of an elongate body 300 having a length of 0.105 inches and a width of 0.28 inches. FIG. 15C illustrates a bottom view of an insert 301 showing recess 624. The insert 301 is inserted into a slot 303 in the elongate body 300, illustrated in FIG. 15D. In this embodiment, the slot 303 has a depth of 0.105 inches and a width of 0.028 inches. FIG. 15E illustrates a side view of the elongate body 300 having a notch 305. When a bone tack 601 is inserted into the distal end 304, as illustrated in FIG. 14, the aperture 607 of the bone tack 601 is exposed to allow an element to pass therethrough. Referring back to FIG. 15E, in this embodiment, the notch 305 has a width of 0.033 inches. It may be appreciated that the dimensions noted herein are examples.

Example methods of installing a bone tack 601 of the present invention are described herein. In one embodiment, a tack 601 of the present invention is mounted in an applicator 620 as described above. An element, such as a lead 610, is threaded through the aperture 607 of the tack 601 while the tack 601 is held in the applicator 620. The tack 601 is inserted into a percutaneous access site, locating the target bone or bony structure via fluoroscopy or other imaging method. The lead 610 is positioned as desired for its intended therapeutic purpose. The bone tack 601 is then tapped into place so that the penetrating end 604 sufficiently penetrates the target bone or bony structure and the head crimps the lead. The applicator 620 is then removed.

Thus, the bone tacks 601 of the present invention can be used to secure various devices without the use of sutures. Further, such securing or anchoring can be achieved in percutaneous procedures without the need for a large surgical exposure. And, such securing and anchoring is easily achievable without excessive manipulation, particularly with the use of the deformable head which secures the lead during insertion of the tack into bone. Likewise, this action is assisted by the use of the applicator which is able to hold the tack and deform the head while inserting the tack into the bone.

Figure 16:
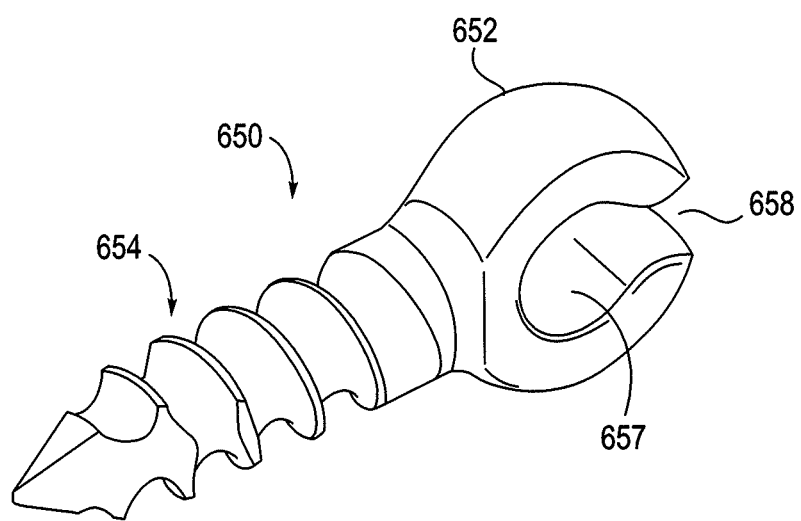
FIG. 16 illustrates an embodiment of a bone screw of the present invention.

FIG. 16 illustrates an embodiment of a bone screw 650 of the present invention. The bone screw 650 can also be used to anchor an element, such as a lead or catheter, to a bone or bony structure near to a site of an intended application. The bone screw 650 has a head 652 and a penetrating end 654 opposite the head 652. Typically, the penetrating end 654 has a tapered shank with a helical thread which is suitable for turning or twisting into bone. In some embodiments, the thread is particularly suitable for penetrating cortical bone. Cortical thread forms are generally finer pitched (more threads per inch) and shallower than thread forms designed to penetrate cancellous bone. In some embodiments, the helical thread has a pitch of 0.020-0.200 inches, more particularly 0.029 inches. Typically, the penetrating end 654 is self-tapping and does not require the use of a bone tap to implant the bone screw 650 into the hard tissue. In some embodiments, the penetrating end 654 has an acute nose angle to assist in self-tapping, such as a 60 degree nose angle. In some embodiments, a wedge is added to further assist in self-tapping, such as a 30 degree wedge.

The head 602 includes an aperture 657 through which the element 152 can be threaded prior to implantation of the element 152 in a manner similar to the bone tack 601 of FIG. 4. Or, the screw 650 can be slipped over a portion of the element 152 through a channel 658 in the head 652 which connects to the aperture 657 in a manner similar to the bone tack 601 of FIG. 7. Optionally, the bone screw 650 may include a grommet having similar features to the grommet 606 described previously in relation to bone tacks 601.

Figure 17A:
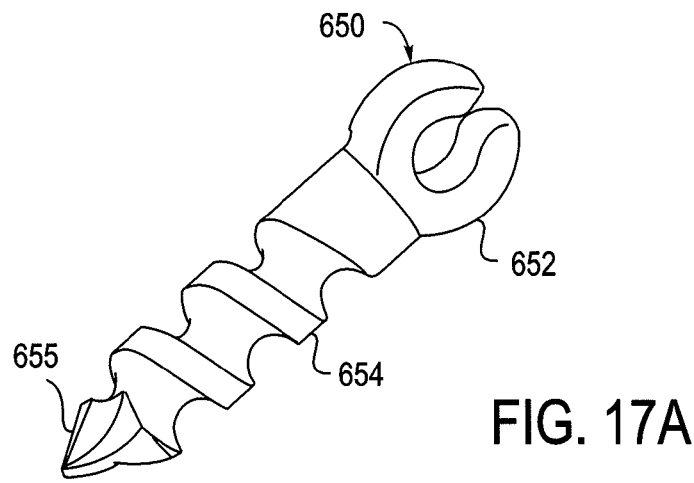
FIGS. 17A, 17B, 17C, 17D, 17E illustrate various view of an embodiment of a bone screw.
Figure 17B:
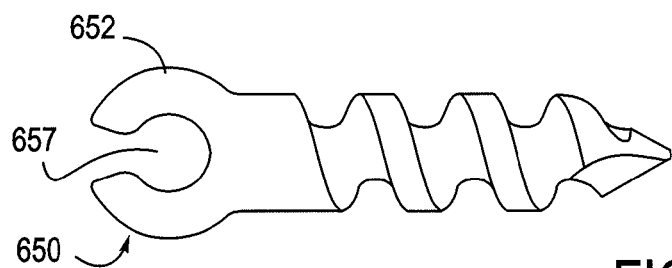
Figure 17C:
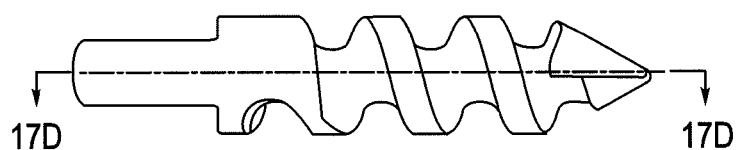
Figure 17D:
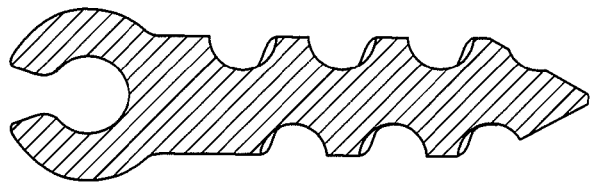
Figure 17E:
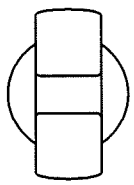

FIGS. 17A-17E provide various views of one embodiment of a bone screw 650 of the present invention. FIG. 17A illustrates a perspective view of a bone screw 650 similar to the bone screw of FIG. 16. However in this embodiment, the penetrating end 654 has a thread which is more suitable for penetrating cancellous bone. FIG. 17B illustrates a side view of the bone screw 650 of FIG. 17A. In this embodiment, the head 652 has a diameter of approximately 0.14 inches and an aperture 657 having a diameter of approximately 0.06 inches. Likewise, the head 652 has a 0.03 inch channel 658. The penetrating end 654 has a length of 0.38 inches from the center of the aperture 657 and a diameter of approximately 0.10 inches (as illustrated in the top view of FIG. 17E). Referring to FIG. 17C and its cross-section shown in FIG. 17D, the penetrating end 654 has a shank with a helical thread with a pitch of 0.075 inches. Thus, the bone screws 650 of the present invention typically have a small size to allow positioning in confined or hard to reach areas of the anatomy. It may be appreciated that such dimensions are exemplary and are not intended to limit the scope of the present invention.

The head 652 and a penetrating end 654 of the bone screws 650 are typically formed from the same material and may comprise any biocompatible and/or bioresorbable material including but not limited to cobalt chromium, cobalt chromium alloys, titanium, titanium alloys, stainless steel, resorbable PGA or PLA, and PEEK.

Figure 18A:
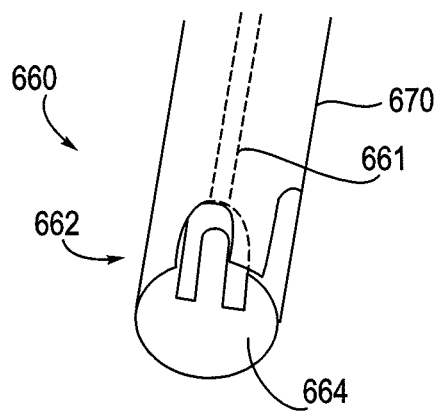
FIGS. 18A-18B illustrate an applicator for delivery of a bone screw to a portion of a hard tissue.
Figure 18B:
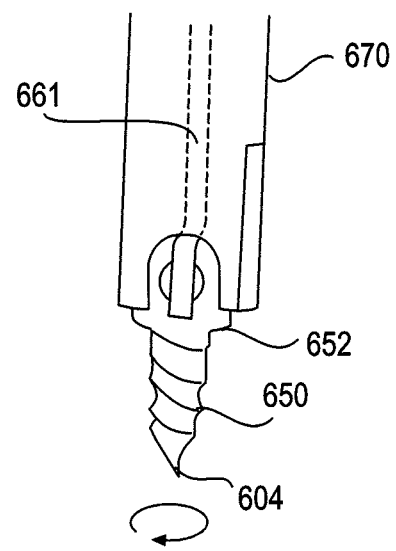

The bone screws 650 of the present invention are driven into a hard tissue, such as a portion of bone B, by rotational force. Referring to FIGS. 18A-18B an applicator 660 is provided for delivery of the bone screw 650 to a portion of a bone B. The applicator 660 is designed similarly to the bone tack applicator 620 in that it has a low profile so that the screw 650 can be delivered through a percutaneous access opening and positioned at an anchoring location via fluoroscopy or other imaging techniques. Again, the applicator 660 typically comprises an elongate body 670 having a proximal end 672 and a distal end 662, wherein the distal end 662 is configured to receive the hard tissue anchor 600. In most embodiments, the applicator 660 also includes a handle attached to the proximal end 672 of the elongate body 670.

FIG. 18A illustrates an embodiment of a distal end 662 of the applicator 660 having a recess 664 for receiving a head 652 of a bone screw 650. The applicator 660 includes a rotatable member 661 which is joinable with the bone screw 650. FIG. 18B illustrates a bone screw 650 securely fixed to the rotatable member 661 via friction, such as with a grommet. The screw 650 is penetrated and anchored into the bone B via rotation of the penetrating end 604 by rotating the member 661. When it is desired to deform or crimp the head 652, force may be applied to the handle and translated to the head 652 which crimps the head 652 onto an element passing through the aperture 657. The screw 650 can then be released from the applicator 660, such as with the use of a release button.

One challenge of a twisting or screw-type penetration is that the orientation of the aperture 657 depends on how the screw 650 is screwed in. Also, placing the lead into the aperture 657 after delivery may be difficult due to its orientation. These challenges are overcome by the bone screws 650 of the present invention. The bone screw 650 may be screwed in place at a desired location first and then the element, such as a lead, is loaded through the channel 658 in the head 652. The lead is then advanced to a desired position for the therapeutic application and secured in place by crimping of the head 652.

Although the foregoing invention has been described in some detail by way of illustration and example, for purposes of clarity of understanding, it will be obvious that various alternatives, modifications and equivalents may be used and the above description should not be taken as limiting in scope of the invention.

What is claimed is:

1. A method for anchoring an element within a body, the method comprising:

positioning the element so that a portion resides within an epidural space of the body and portion resides outside of the epidural space;

placing a penetrating end of a hard tissue anchor against a surface of a bone, wherein the penetrating end has a shape configured for penetrating bone, and then applying force to drive the penetrating end of the hard tissue anchor into the surface of the bone;

fixing the portion of the element residing outside of the epidural space to a head of the hard tissue anchor so as to substantially maintain the position of the element;

wherein the element comprises a lead having at least one electrode and positioning comprises positioning the at least one electrode within the epidural space;

wherein the head includes a channel connected to an aperture and further comprising passing a portion of the element through the channel to the aperture; and wherein fixing comprises deforming the head so as to at least partially close the channel.

2. A method as in claim 1, wherein the surface of the bone is adjacent a point of entry of the element into the epidural space.

3. A method as in claim 1, wherein the surface of the bone is on a spinous process of a vertebrae.

4. A method as in claim 1, wherein the surface of the bone forms at least part of a foramen.

5. A method as in claim 1, wherein positioning comprises positioning at least one of the at least one electrodes so as to selectively stimulate a dorsal root ganglion.

6. A method as in claim 1, wherein positioning comprises positioning the element so that at least a portion of the element resides within a foramen.

7. A method as in claim 1, wherein fixing comprises applying pressure to the head so as to secure the element within the aperture.

8. A method as in claim 7, wherein applying pressure comprises deforming the head so as to secure the element within the aperture due to friction.

9. A method as in claim 1, wherein the applying and fixing steps occur at least partially simultaneously.

10. A method as in claim 1, wherein applying force comprises advancing a distal end of an applicator having the hard tissue anchor mounted thereon so as to drive the penetrating end into the surface of the bone.

11. A method as in claim 10, further comprising advancing the distal end of the applicator through a percutaneous access opening.

* * * * *